(12) United States Patent
Craighead et al.

(10) Patent No.: US 6,559,474 B1
(45) Date of Patent: May 6, 2003

(54) METHOD FOR TOPOGRAPHICAL PATTERNING OF MATERIALS

(75) Inventors: Harold G. Craighead, Ithaca, NY (US); Bojan Ilic, Ithaca, NY (US)

(73) Assignee: Cornell Research Foundation, Inc,, Ithaca, NY (US)

( * ) Notice: Subject to any disclaimer, the term of this patent is extended or adjusted under 35 U.S.C. 154(b) by 0 days.

(21) Appl. No.: 09/955,413

(22) Filed: Sep. 18, 2001

Related U.S. Application Data

(60) Provisional application No. 60/233,377, filed on Sep. 18, 2000.

(51) Int. Cl.[7] .................................................. H01L 35/24
(52) U.S. Cl. ................................... 257/40; 435/6; 435/5
(58) Field of Search .............................. 257/40; 435/5, 435/6

(56) References Cited

U.S. PATENT DOCUMENTS

| | | |
|---|---|---|
| 5,315,880 A | 5/1994 | Bailey |
| 5,463,402 A | 10/1995 | Walrath et al. |
| 5,537,124 A | 7/1996 | Rankin, Jr. et al. |
| 5,968,745 A | * 10/1999 | Thorp et al. |
| 6,239,019 B1 | * 5/2001 | Chiang et al. |

OTHER PUBLICATIONS

Analog Devices, Inc. product literature.

* cited by examiner

*Primary Examiner*—Petsum Abraham
(74) *Attorney, Agent, or Firm*—Schwegman, Lundberg, Woessner & Kluth, P.A.

(57) ABSTRACT

A method of patterning a preselected material on a substrate is provided, comprising coating a substrate surface with a releasable polymer coating, creating one or more openings through the polymer coating to expose a portion of the substrate surface in a predefined pattern, coating at least a portion of the substrate surface that is exposed through the polymer coating with at least one preselected material, and optionally, removing said polymer coating so that the material is retained on said substrate surface in said predefined pattern.

21 Claims, 11 Drawing Sheets

METHOD FOR TOPOGRAPHICAL PATTERNING OF MATERIALS

This application claims priority under 35 U.S.C. 119(e) to U.S. Provisional patent application Ser. No. 60/233,377, filed Sep. 18, 2000, which is incorporated herein by reference.

TECHNICAL FIELD

The invention relates generally to material processing and, more particularly, the invention pertains to a method for producing preselected patterns of biochemical materials on substrate surfaces, and the patterned substrates produced thereby.

BACKGROUND OF THE INVENTION

A great deal of consideration has been given in recent years to the chemical and biological uses of micro and nanoelectromechanical systems (MEMS and NEMS). For example, see R. F. Taylor, in *Handbook of Chemical and Biological Sensors*, R. F. Taylor et al., eds., Institute of Physics Publishing, Bristol, UK (1996) at page 553; R. J. Foster, in *Principles of Chemical and Biological Sensors*, D. Diamond, ed., John Wiley and Sons, Inc. N.Y. (1998) at p. 235; A. F. Collings et al., *Rep. Prog. Phys.*, 60, 1397 (1997); B. Ilic et al., *Appl. Phys. Lett.*, 77, 450 (2000); D. W. Carr et al., *J. Vac. Sci. Technol. B*, 16, 3821 (1998) and S. Turner et al., op. cit., 15, 2848 (1997). Physical sensors, in general, are based on a mature technology and have many commercial manifestations, however, biological sensor technology is still emerging and few commercial products are found in the clinical setting. For example, see I. Amato, *Technology Rev.*, 74 (1999); L. J. Kricka, *Nature Biotech.*, 16, 513 (1998). One of the crucial features in the fabrication of effective biosensors is the development of immobilization technologies for stabilizing biomolecules and tethering them to surfaces in selected device areas. The ability to generate mesoscopic (0.1 $\mu$m–10 $\mu$m) area patterns of biological materials offers new applications for these engineered biomolecular surfaces in the field of cell culturing, tissue engineering, biosensor technology, drug discovery, and nanotechnology. For example, see R. Singhui et al., *Science*, 204, 696 (1994); E. Delmarche et al., *Science*, 276, 779 (1997); C. S. Chen et al., op. cit., at page 1425; C. D. James et al., *Langmuir*, 4, 741 (1998); S. Takayama et al., PNAS USA, 96, 5545 (1999); P. M. St. John et al., *Anal. Chem.*, 70, 1108 (1998); M. J. Feldstein, *J. Biomed. Microdevices*, 1, 139 (1999); and R. Kapur et al., op cit., 2, 99 (1999).

Microcontact printing ($\mu$CP) can be used as a parallel lithography technique for localized geometric confinement of self-assembled monolayers (SAM), as well as various chemically sensitive polymers and biological materials. For example, see, H. A. Biebuyck et al., *IBM J. Res. Devel.*, 41, 159 (1997); N. B. Larsen et al., *JACS*, 119, 3017 (1997); I. Yan et al., *JACS*, 120, 6179 (1998); B. A. Grzybowski et al., *Anal. Chem.*, 70, 4645 (1998); P. Yang et al., *Science*, 282, 2244 (1998) and E. Delmarche et al., *J. Phys. Chem. B*, 102, 3324 (1998). The method is based on utilizing a "stamp" made from poly(dimethylsiloxane) (PDMS) elastomer to transfer biological material so as to form a layer of patterned material on the surface of a substrate by a covalent chemical reaction. The patterns serve as an etch mask to subsequent chemical etching of the underlying layer. Submicrometer features over areas greater than 1 cm$^2$ have been etched in gold using microcontact printing. There are, however, several drawbacks with $\mu$CP, such as pairing and sagging of the stamp, evolving from the elastomeric properties of PDMS (Y. Xia et al., *Angew. Chem. Int. Ed.*, 37, 550 (1998)). Furthermore, PDMS tends to shrink upon curing and swell when in contact with nonpolar solvents.

Thus, a need exists in the art for new approaches to patterning biological materials on solid surfaces that allow for proper placement and consistent and repeatable patterning, under processing conditions that do not limit or destroy the biological materials being patterned on the surface.

SUMMARY OF THE INVENTION

The present invention provides a method of patterning a wide variety of inorganic and organic materials, and is particularly well-adapted to pattern biological materials on a substrate comprising coating a substrate surface with a releasable polymer coating, creating one or more openings through the polymer coating to expose a portion of the substrate surface in a predefined pattern, coating at least a portion of the substrate surface that is exposed through the polymer coating with at least one preselected material, such as a metal or a biological material, and optionally removing said polymer coating so that the material is retained on said substrate surface is said predefined pattern.

Thus, the present invention provides a method that accomplishes the proper placement and the consistently repeatable patterning of materials on target surfaces. The patterning is carried out under processing conditions that do not inhibit or destroy the material that is patterned on the surface. For example, the present invention also provides an efficient and economical method of producing micrometer sized patterns of cells or other biomaterials over large areas.

A preferred embodiment of the present method can be referred to as a "dry lift-off" method that allows patterning of chemically sensitive materials, such as biological materials, on a variety of surfaces. Using a combination of projection lithography and reactive ion etching, a surface coated with an inert flexible polymer is patterned and subsequently coated with a layer of one or more preselected materials. The polymer film is peeled from the substrate surface and the desired pattern of residual material is formed. The present method is exemplified by the production of silicon wafers patterned with antibodies, poly-L-lysine and aminopropyltriethoxysilane (APTS) self-assembled monolayers. These surfaces were respectively used to pattern *Escherichia coli* serotype O157:H7 bacteria cells, rat basophilic leukemia (RBL) cells and 20 nm diameter aldehyde-sulfate coated fluorescent polystyrene beads. Typical patterns consisted of arrays of 5 mm long parallel lines of bacteria confined to stripes with widths varying from 2 $\mu$m to 20 $\mu$m. Such pattern can be made over large areas, e.g., areas up to 3 cm$^2$ or greater.

The present method permits the construction of geometrically well-defined regions of materials such as biochemicals, tissues and cells. The present method offers several advantages over traditional cell patterning methods. The present microfabrication techniques pattern a chemically inert polymer with a high degree of dimensional control in order to shape and confine the layer of preselected material. Using a polymer that is both chemically inert and thermally stable over a wide range of temperatures, permits the selective immobilization of a wide variety of materials, such as biologicals, and any other chemically sensitive materials.

The method provides an efficient and economically practical technique to reproduce micrometer sized patterns over areas spanning many cm$^2$. One of the desirable and significant applications of this technology is to develop new types of rapid detection, fully integrated, high sensitivity, biological sensors and systems for screening of pharmaceuticals, detection of toxins, microanalysis of proteins, and DNA sequencing. For instance, the present method can readily integrate bioMEMS and bioNEMS devices with the complementary metal oxide semiconductor (CMOS) post-processing technology, thus enabling highly flexible, reproducible, high yield, low cost, batch fabrication of smart biological sensors. For example, see, Y. T. C. Yeh et al., *J. Vac. Sci. Technol. A*, 2, 604 (1983); D. T. Price et al., *Thin Solid Films*, 309–309, 523 (1997) and S. Rogojevic et al., *J. Vac. Sci. Technol. A*, 17, 266 (1999).

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

DESCRIPTION OF THE EMBODIMENTS

Figure 1:
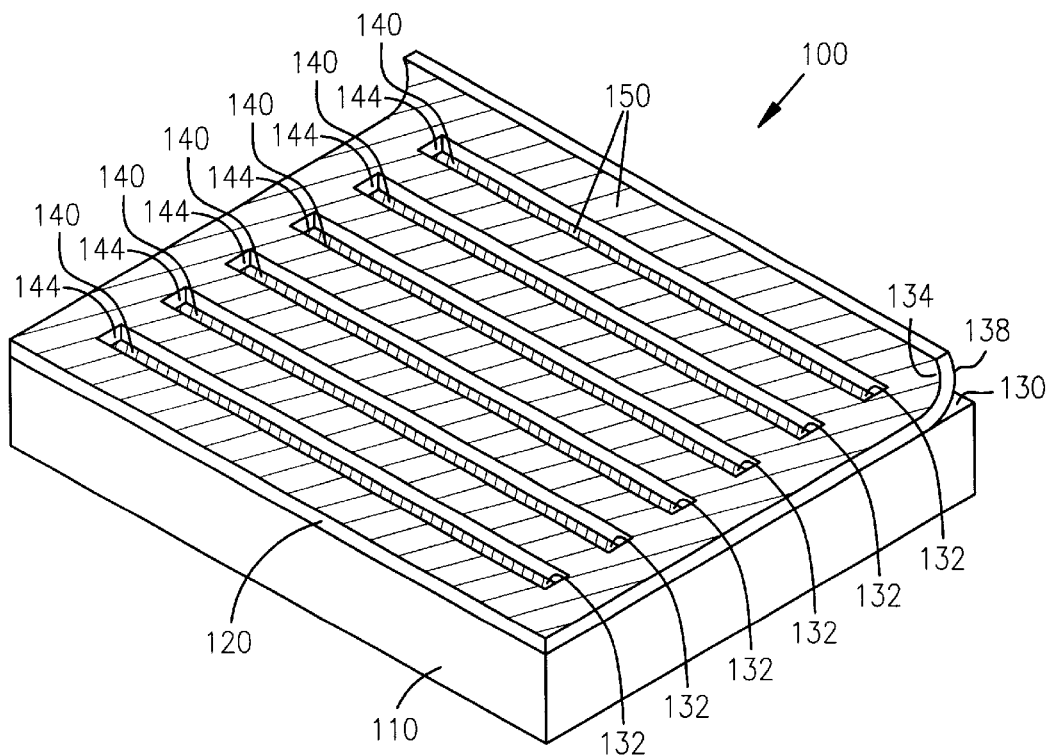
FIG. 1 is a schematic, in perspective view, of an apparatus according to one embodiment of the present invention.

The present invention allows for the precise manipulation and placement of a wide variety of preselected materials, including biological materials, such as peptides and/or cells, on a substrate. The terms "preselected materials" and "biological materials" as used herein are intended to be defined broadly. The term "biological materials" can encompass organic chemicals and compositions, such as synthetic and natural polymers, including tissues, cells, cellular subunits and cellular products. Such materials include bacterial yeast, insect, fungal, mammalian and plant cells and their products and components. Thus, isolated entities or "biologicals" include nucleic acids and polypeptides, i.e., receptors, cytokines, antibodies, antigens and the like. Other useful materials include inorganic materials or organometallic materials, such as metals, catalysts, and the like that can be coated onto the polymeric "stencil" layer without degrading it. The present method has been used to define patterns (e.g., lines and dots) of metal, such as chromium and gold.

Both the control over and the precise placement of materials such as biological materials on substrates are important aspects in the areas of bimolecular surface engineering and the study of cell behavior. In addition to these aspects, the present invention is an important advance in the area of chemical sensor and biological sensor technology. A crucial feature in the development and fabrication of chemical sensors, biological sensors and devices for cell-based drug screening is the development of immobilization technologies for patterning and stabilizing biomolecules on substrate surfaces. The ability to generate patterns of biological materials having pattern widths on the mesoscopic (0.1 micrometer to 10 micrometer) scale offer the potential of yielding engineered bimolecular surfaces useful in the fields of cell culture, tissue engineering, biosensor technology, medicine, and micro and nanotechnology.

The present invention also provides a method for forming micrometer sized patterns having sensitive bimolecular surfaces, on substrates using a polymer based "dry lift-off" technique, as well as the patterned substrates formed thereby. In general, the lift-off of the polymer involves the formation of a photolithographically defined photoresist layer. The photoresist layer is formed prior to the deposition of the layer that defines the desired pattern. The portions of the surface that are deposited on the photoresist layer are removed during subsequent dissolution of the photoresist, and the desired pattern on the polymer is formed. An advantage in the present dry lift-off polymer surface for forming the micrometer sized patterns, that is solvents which deleteriously effect biological molecules are not used. Thus, the present invention can be used to pattern chemically sensitive polymers and bimolecular materials that cannot be patterned with other patterning techniques.

Thus, the present invention provides a substrate comprising a surface that is coated with a polymer coating, where the polymer coating is releasably attached to the substrate surface. The polymer coating further includes one or more predefined openings through which portions of the substrate are exposed in a predefined pattern. The polymer coating has walls that define wells along the predefined openings. The openings forming the wells preferably have micrometer scale dimensions. These wells formed by the predefined openings in the polymer film are adapted to leave the preselected material in a predefined pattern on the substrate surface, once the polymer film has been removed.

The one or more predefined openings in the polymer coating can be created in a number of ways. For example, the openings through the polymer coating can be created through the use of photolithography and dry etching of the polymer coating. In this process, the pattern of openings is defined by photolithography using an ultraviolet sensitive photoresist. The polymer coating can then be dry etched in a reactive ion etch chamber using plasma. Alternatively, patterning the predefined openings in the polymer coating can be accomplished by a variety of modern lithography techniques, including electron beam lithography. The result is a pattern of predefined openings through which portions of the substrate are exposed. A preselected material can then be applied to both the polymer coating and the portions of the substrate exposed in the predefined pattern, as by vapor deposition or electron beam evaporation techniques. The material is allowed to form a layer at least on a portion of, and preferably, a major portion of, the substrate exposed in the predefined pattern. The polymer coating is then removed from the substrate, e.g., it is peeled off substantially intact, resulting in the immobilized material, i.e., a biological material (e.g., an antibody-antigen complex) remaining on the substrate in the pattern of the predefined openings.

As used herein, the term "microscale" or "microfabricated" generally refers to structural elements or features of a device which have at least one fabricated dimension in the range of from about 1 $\mu$m–1 mm. Thus, an apparatus referred to as being microfabricated or microscale will generally include at least one structural element or feature having such a dimension. However, the present process is compatible with structures outside of these dimensions, e.g., in excess of several centimeters.

FIG. 1 is an illustration of an apparatus 100 according to the present invention. The apparatus 100 comprises a substrate 110 and a polymer coating 120 on the substrate 110, where the relative dimensions of the substrate 110 and the polymer coating 120 are not to scale. The polymer coating 120 is releasably attached to the substrate 110, so that the polymer coating 120 can be completely removed (e.g., peeled off) from the substrate 110 by methods available to the art. This aspect of the interaction between the substrate 110 and the polymer coating 120 is shown generally at 130 in FIG. 1.

The polymer coating 120 further includes one or more predefined openings 132 between a first surface 134 of the polymer coating 120 and a second surface 138 of the polymer coating, where the first surface 134 is opposed to the second surface 138. The openings 132 allow a portion 140 of the substrate 110 to be exposed through the openings 132. The openings 132 include walls 144 that define the shape of the openings 132. The walls 144, along with the exposed substrate surface, further define wells along the predefined openings into which fluids, including fluids comprising binding peptides, can be placed and retained for the necessary amount of time. The openings forming the wells have micrometer scale dimensions, e.g., the openings can have widths in the range of at least about 0.1 $\mu$m, e.g., from about 0.1 to 20 micrometers to any preselected dimension. These wells formed by the predefined openings in the polymer film and the exposed surface are adapted to define biological materials in a predefined pattern on the substrate 110. In one embodiment of the invention, the openings 132 are etched into the polymer coating 120, as will be described in greater detail below. In addition to etching the polymer coating 120 to create the openings 132, the substrate 110 exposed thought the predefined openings 132 can also be etched or otherwise partially removed so as to create a well or depression in the surface of the substrate 110.

The apparatus 100 further includes a peptide layer 150 (shown in cross-hatch in FIG. 1) on the first surface 134 of the polymer coating 120 and on the portion 140 of the substrate 110 that is exposed through the predefined openings 132. The junction between the second surface 138 of the polymer coating 120 and the substrate 110 is fluid tight, so peptide 150 is not between the second surface 138 and the substrate 110. In addition, the exposed portion 140 of the substrate surface 110 can be treated to allow the surface 140 to be more easily wettable (i.e., to produce a reduction in surface tension in the fluids used to carry a material such as a protein and/or peptide so as to allow better wetting of the exposed portions 140 of the substrate 110).

The substrate 110 can be any number of materials that comprise a relatively smooth surface, so that the polymer coating can be completely and readily removed therefrom. For example, materials used as the substrate 110 can include, but are not limited to, single crystalline materials, such as silicon or quartz, or various group II/V materials, such as gallium arsenide. Other possible substrate materials include silica, glass, ceramics, metals (e.g., gold or chromium), plastics and semi-conductors. The substrate 110 can include two or more materials such that the two or more materials are presented on the surface of the substrate 110. In an additional example, the substrate is classified as a complex substrate that can include, but is not limited to, one or more components of an electronic integrated circuit, integrated optical devices and/or fluidic channels.

The polymer coating 120 can be formed from any number of conformal polymer materials. Basic characteristics of conformal polymers that are useful with the present invention include the formation of a void-free and pin-hole free surface that forms a fluid tight bond between the polymer and the substrate, but yet is releasable from the substrate through the use of mechanical force (e.g., peeling or lifting the polymer coating from,the substrate). The conformal polymer must also have sufficient physical characteristics to allow for precisely defined openings to be created and maintained in predetermined patterns through the polymer, and must not be degraded or destroyed by application of the preselected material and any carrier.

Examples of conformal polymers that can fulfill these requirements include elastomers such as the polyaromatics. An example of a polyaromatic that can be used in the present invention is Parylene. Parylene is both chemically inert and thermally stable over a wide range of temperatures. For example, see, W. H. Gorham, *J. Polym. Sci.*, 4, 3027 (1966); M. A. Spivak, *Rev. Sci. Inst.*, 7, 985 (1972); T. E. Baker et al., *J. Electrochem. Soc.*, 124, 897 (1977); M. A. Spivak et al., *J. Electrochem. Soc.*, 116, 1592 (1964); S. Ganguli et al., *J. Vac. Sci. Technol. A*, 15, 3138 (1997). These properties allow for a wide variety of bimolecular materials and chemically sensitive layers to be immobilized on the substrate surface. Other inert polymers that can be conformally deposited can also be used in the present invention, such as the polyalkylenes.

The biological materials for forming the layer 150 can be selected from peptides that promote the adhesion of the cells. The peptides can also promote the growth and proliferation of the cells. Example of peptides used to create the adhesive layers include, but are not limited to, antibodies and antibody subunits and fragments, adhesive proteins and/or peptides, including adhesive glycoproteins and cellular adhesive types of collagen.

Once the substrate 110 and the polymer coating 120 have been coated with the peptide layer 150, the apparatus 100 can be processed in at least two different manners. In a first manner, the apparatus has its polymer coating 120 removed from the surface of the substrate 110, leaving the peptide layer 150, in the pattern of the openings 132 on the surface of the substrate 110. The substrate 110, with its patterned peptide layer 150, can then be incubated with cells so as to allow the cells to adhere to the peptide layer 150 to form a patterned layer of cells. In the second manner, cells are incubated with the apparatus 100 to allow the cells to adhere to the peptide layer 150. The polymer coating 120 is then removed from the surface of the substrate 110 to leave cells in the pattern of the openings 132 on the surface of the substrate 110.

Figure 2:
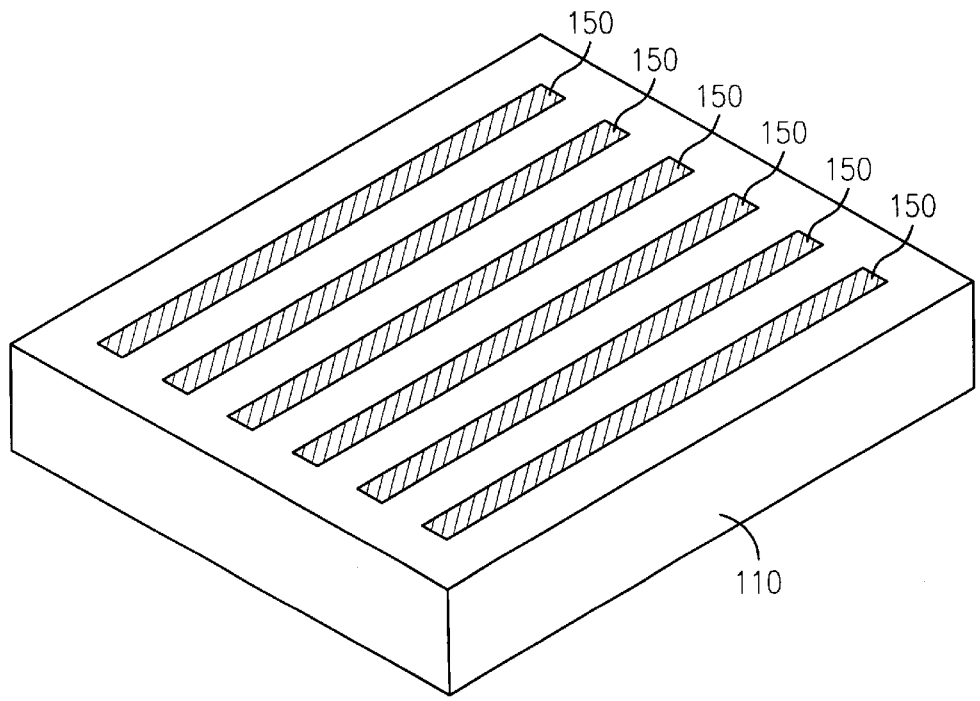
FIG. 2 is a schematic, in perspective view, of a substrate with a patterned peptide layer according to one embodiment of the present invention.

FIG. 2 shows one embodiment of substrate 110 after the polymer coating 120 has been removed from the apparatus 100 shown in FIG. 1. Peeling can be accomplished at the periphery of the substrate surface (away from the desired pattern and close to the edge) by applying a tab or handle that adheres to the polymer surface and extends beyond the edge of the surface. The polymer is then peeled away from the surface by pulling the tab or handle away from the substrate, thus separating the polymer layer from the surface. The tab can be as simple as a strip of adhesive tape.

As depicted in FIG. 2, the peptide layer 150 is on the substrate 110 surface in the pattern of the openings 132, as shown in FIG. 1. Furthermore, the polymer coating 120 can be removed from the substrate 110 without disrupting the pattern of the peptide layer 150 defined by the openings 132.

Once the polymer coating 120 is removed, a wide variety of cells can be added to and incubated on the substrate 110, so that the cells selectively adhere to the peptide layer 150. Once the cells have been incubated on the substrate 110 for sufficient time to adhere to the peptide layer 150, non-specifically bound cells are washed or otherwise removed from the substrate 110 surface, to leave only the cells adhering to the peptide layer 150 on the substrate 110.

In addition to the pattern shown in FIG. 2, peptide layers in a variety of other patterns can be formed on the substrate 110. For example, openings in the polymer coating can define areas that have one or more curves, arcs, or bends. These openings may or may not intersect with each other or with other openings in the polymer coating. In addition, peptide "pathways" between two or more points on the substrate 110 can be created having any number of straight segments, bends and/or turns which provide the desired area of peptide layer coverage and/or the shortest path or most efficient pathway between the two points.

It is also possible to provide a substrate with a first material in a first pattern and a second material in a second pattern. For example, a first pattern can be etched into a first polymer layer and coated with a first material. The polymer layer can be removed and the first pattern can be re-coated with Parylene or another polymer. A second pattern can be etched into the second polymer coating, which then can be coated with a second material. The polymers can then be removed to yield a substrate with two patterned materials where each material has its own distinct pattern. Using this technique, substrates can also be patterned with more than two materials.

Figure 3:
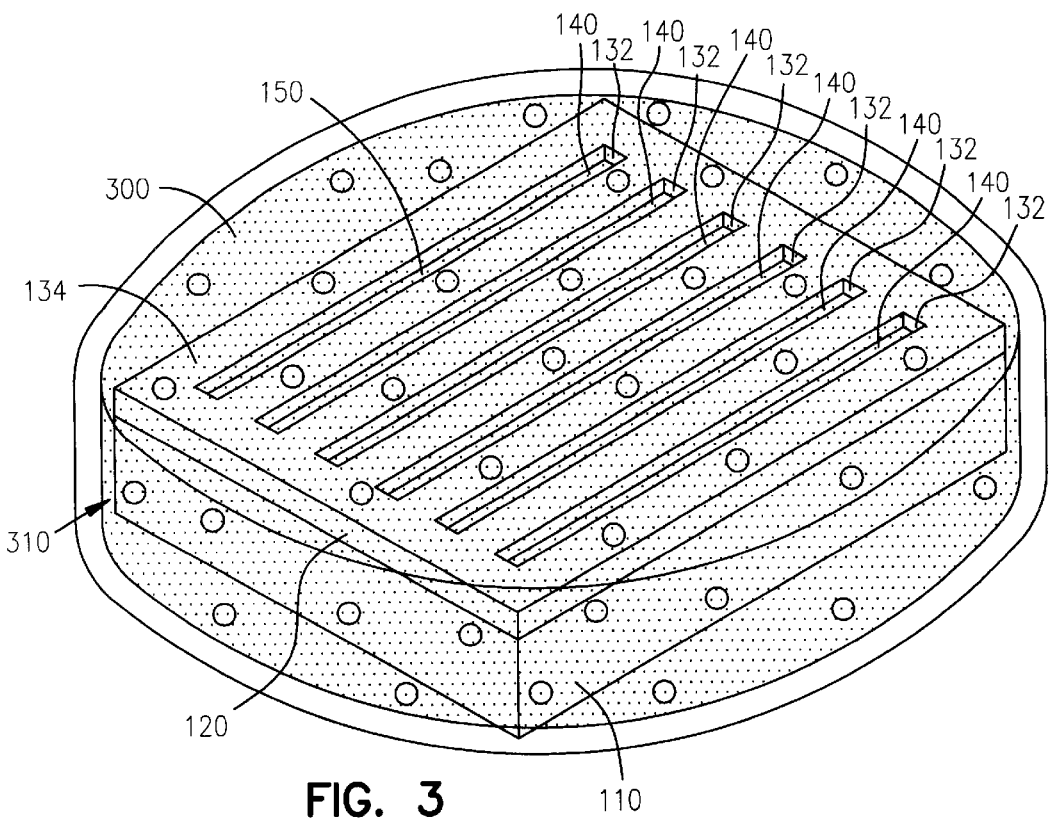
FIG. 3 is a schematic, in perspective view, of an apparatus according to one embodiment of the present invention.

FIG. 3 is an additional illustration of the apparatus 100 according to the present invention. The apparatus 100 shown in FIG. 3 is identical to that shown in FIG. 1. The apparatus of FIG. 3, however, further includes cells 300 added to the apparatus 100 prior to the removal of the polymer coating 120. The cells are added to the apparatus 100 by placing biological cells in a liquid suspension 310 and then plating the cells onto the first surface 134 and the portions 140 of the substrate 110. The liquid suspension 310 in which the cells are delivered can include, but is not limited to, various culture media, as are adapted to a given cell type.

Figure 4:
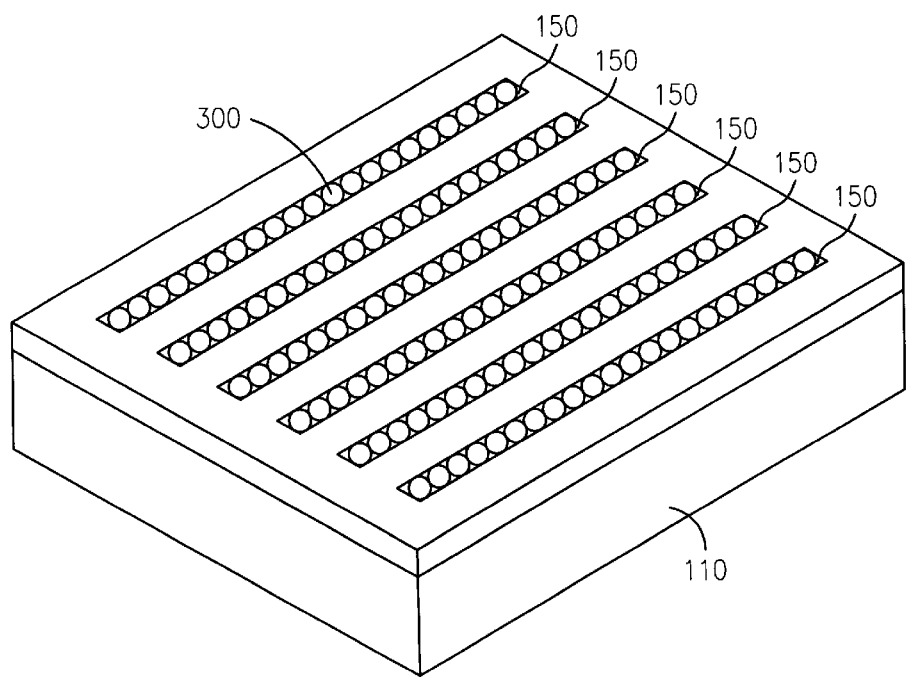
FIG. 4 is a schematic, in perspective view, of a substrate with a patterned peptide and biological cell layer according to one embodiment of the present invention.

The cells 300 are then incubated with the apparatus 100 to allow the cells to adhere to the peptide layer 150. Once the cells 300 have adhered to peptide layer 150, the polymer coating 120 is removed from the substrate 110 to leave the cells 300 on the substrate 110 in the pattern of the predefined openings 132 through the polymer coating 120. As with the peptide layer 150 described above, the polymer coating 120 can be removed from the surface of the substrate to leave the cells 300 on the surface of the substrate 110 in the pattern of the predefined openings 132 through polymer coating 120. FIG. 4 shows an example of the substrate 110 having cells 300 adhered to the peptide layer 150 in the pattern of the predefined openings 132.

The predefined openings 132 can have any number of shapes and/or dimensions. For example, the predefined openings 132 can be created that conform closely to the diameter of the cells or to an undetermined number of cells. In such cases, some of the applied cells that overlap the edge of the opening will be removed from the substrate surface when the polymer is lifted off. The openings in the polymer coating can define areas which are dotted, linear, have one or more curves, arcs, or bends, have one or more intersections between other and/or the same openings. This list of opening shapes is presented as examples of possible shapes and should not be taken as limiting. Furthermore, the present invention provides an efficient and economical method to repeatably produce micrometer-sized, geometrically-well defined patterns of biological materials over substrates having a variety of surface areas. For example, using the present invention patterns of biological materials can be applied to substrates having surface areas of three (3) square centimeters.

Figure 5:
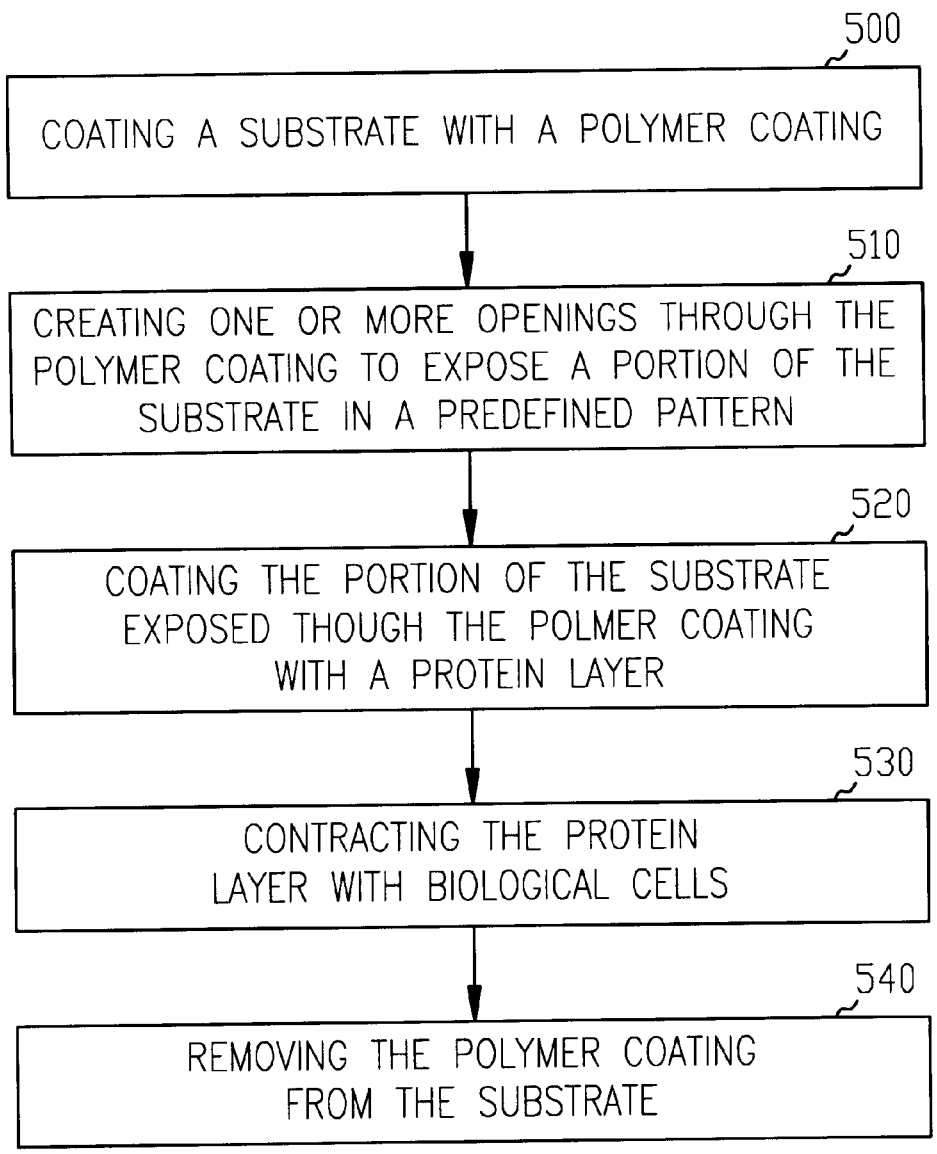
FIG. 5 is a flow chart of a method according to one embodiment of the present invention.

FIG. 5 show a flow chart of an exemplary method according to the present invention. At 500, the substrate is coated with the polymer coating, where the polymer coating and the substrate are as previously described. At 510, one or more openings are created the through the polymer coating to expose portions of the substrate in the predefined pattern. See Y. T. C. Yeh et al., *J. Vac. Sci. Technol. A*, 1, 604 (1983); D. T. Price et al., *Thin Solid Films*, 308–309, 523 (1997). In one example, an ion etching process is used to create the one or more openings through the polymer coating to expose the substrate in the predefined pattern. As previously discussed, etching creates wells in the exposed substrate into which biological materials, such as peptides and/or cells, can be placed. At 520, the portions of the substrate that are exposed though the polymer coating are then coated with the peptide layer. As previously discussed, the walls of the patterned Parylene layer combine with the exposed surface to define a well or channel to physically position deposited peptides, biological cells and other materials. At 530, the peptide layer is contacted with at least one population of biological cells at 530, so that the biological cells are adhered to the peptide layer. Once the cells have adhered to the peptide layer, the polymer coating is removed from the substrate at 540 so as to leave the cells on the peptide layer along the predefined pattern on the substrate surface and create preselected patterns of adhered cells.

One of the desirable and significant applications of the present invention is to develop rapid detection, fully integrated, high sensitivity, biological sensors, actuators and devices for screening of pharmaceuticals, detection of toxins, microanalysis of protein and DNA sequencing, along with other applications. Other applications for the present invention include its use in the development and integration of bioMEMS and bioNEMS devices with complementary metal oxide semiconductors (CMOS) in post-processing technology. This can yield highly flexible, reproducible, high yield, low cost, batch fabrication of smart biological sensors. The ability to register or orient the openings in the polymer coating with respect to features and structures on the substrate surface can be accomplished by the described and/or suggested lithographic approaches. This is important for placing bioactive or other patterned layers (e.g., metal such as gold or chromium) in the desired patterns and/or places so as to functionally connect components of the device. A key aspect of the present invention is the ability to produce micrometer and submicrometer patterns of biological materials using a releasable polymer coating that is thermally stable and biologically and chemically compatible with the cells used with the method and apparatus.

As one example, a chemical sensor, prepared using this technique, can be incorporated with CMOS elements. First CMOS elements are fabricated on a silicon substrate. Then platinum electrodes are integrated with the CMOS elements. The surface is then passivated using a polymer coating, e.g., of Parylene. The Parylene is then patterned over the active area of the platinum electrodes. An electrolyte is then deposited over the substrate. Parylene is peeled leaving behind electrolyte only over the active area, thus forming an electrochemical sensor for the detection of hazardous gases that is integrated with CMOS elements.

In general, one method of creating the predefined openings in the polymer coating involves the formation of a photolithographically defined photoresist layer prior to deposition of the layer in which patterning is desired. Those portions which are deposited on the photoresist layer are removed during subsequent dissolution of the photoresist, to form the desired pattern. As the present apparatus and method do not utilize solvents which degrade biological molecules, the apparatus and method can be used to pattern chemically sensitive substrates and peptide layers.

EXAMPLE 1

Utilizing a Photolithographically Defined Photoresist Layer on a Polymer Coating to Create a Patterned Cell Layer The substrates were a two (2) inch<111>p-doped prime grade silicon wafers having 6–15 ohm-cm resistivity. The wafers were cleaned in piranha solution (3 $H_2SO_4$: 1 $H_2O_2$) for 10 minutes and then rinsed in deionized water and dried under nitrogen gas. The wafers were then coated with a 1 $\mu$m thick conformed film of Parylene using a Model PDS-2010 Labcoater 2 Parylene deposition system (Specialty Coating Systems, Indianapolis, Ind.). To coat each wafer, the wafer was placed in the vapor-phase deposition chamber and a vacuum of approximately 10 mTorr to 100 mTorr was applied.

Parylene C, initially supplied as a granular dimer (di-para-xylylene), was loaded into the vaporizer which was heated to approximately 175° C. The gaseous Parylene C dimer was then heated to a 690° C., causing pyrolysis (cleavage of the dimer to a monomer). The para-xylylene monomer condensed on the wafer in the deposition chamber, which is at 25° C., and polymerized thereupon to form a thin film of poly-para-xylylene.

Optical UV photolithography was used to define the one or more openings in the polymer coating. FIGS. 6A–6D shows a schematic representation of the processing stages of patterning, etching, coating and exposing the wafer to cells and removing the polymer coating. First, the wafer and a solution of hexamethyldisilane (HMDS) were spun at 4000 rpm for 10 seconds to achieve adhesion between the Parylene and the photoresist film. Immediately following, OGC 897-12i positive photoresist and the treated wafer were spun at 4000 rpm for 30 seconds. The wafer was then pre-baked at 90° C. for five minutes. Using a GCA 630 DSW 10x i-line (365 nm) Stepper, the photoresist was exposed through a photomask having the predefined pattern of the one or more openings with ultraviolet light for 1.2 seconds with a focus setting of 254.

Figure 6A:
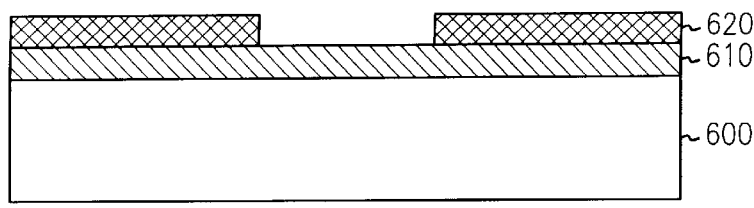
FIGS. 6A, 6B, 6C and 6D are a process flow schematic of a method of forming a patterned antibody and attached cell layer on a substrate according to one embodiment of the present invention; (6A) photoresist patterning using optical lithography; (6B) reactive ion etching of Parylene and removal of the top photoresist layer; (6C) *E. coli* antibody and cell immobilization; (6D) peeling of the Parylene, resulting in an antibody-cell pattern.

The photoresist was then developed in a CD-26 developer solution for 90 seconds. FIG. 6A shows the substrate 600 at this stage of the process, where the substrate 600 includes the polymer coating 610 and the patterned photoresist layer 620. The wafer was then rinsed in deionized water and dried under nitrogen gas. For patterns extending beyond 1 $cm^2$, a Karl Suss MA-6 contact aligner was used to expose the Parylene covered silicon wafers.

Figure 6B:
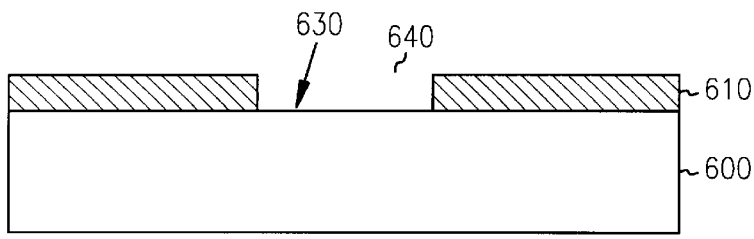

The Parylene film is etched away in a reactive ion etch (RIE) chamber using oxygen ($O_2$) plasma (FIG. 6B). Due to the hydrophobic nature of silicon, an oxygen plasma treatment was found to be necessary in order to facilitate successful immobilization of the peptides on the exposed surface of the substrate. In addition, a slightly over-etch of the Parylene was carried out in order to oxidize a thin top silicon layer to enhance peptide (e.g., antibody) adhesion.

The plasma etch parameters were 30 sccm $O_2$ flow, forward power of 150 W, 60 mTorr chamber pressure for 5 minutes. The wafers were then rinsed in acetone to dissolve the residual photoresist, then in isopropyl alcohol, and in de-ionized water, and finally dried under nitrogen gas. FIG. 6B shows the substrate after this process, where a portion 630 of the substrate 600 is exposed through the etched opening 640 in the polymer coating 610.

Figure 7A:
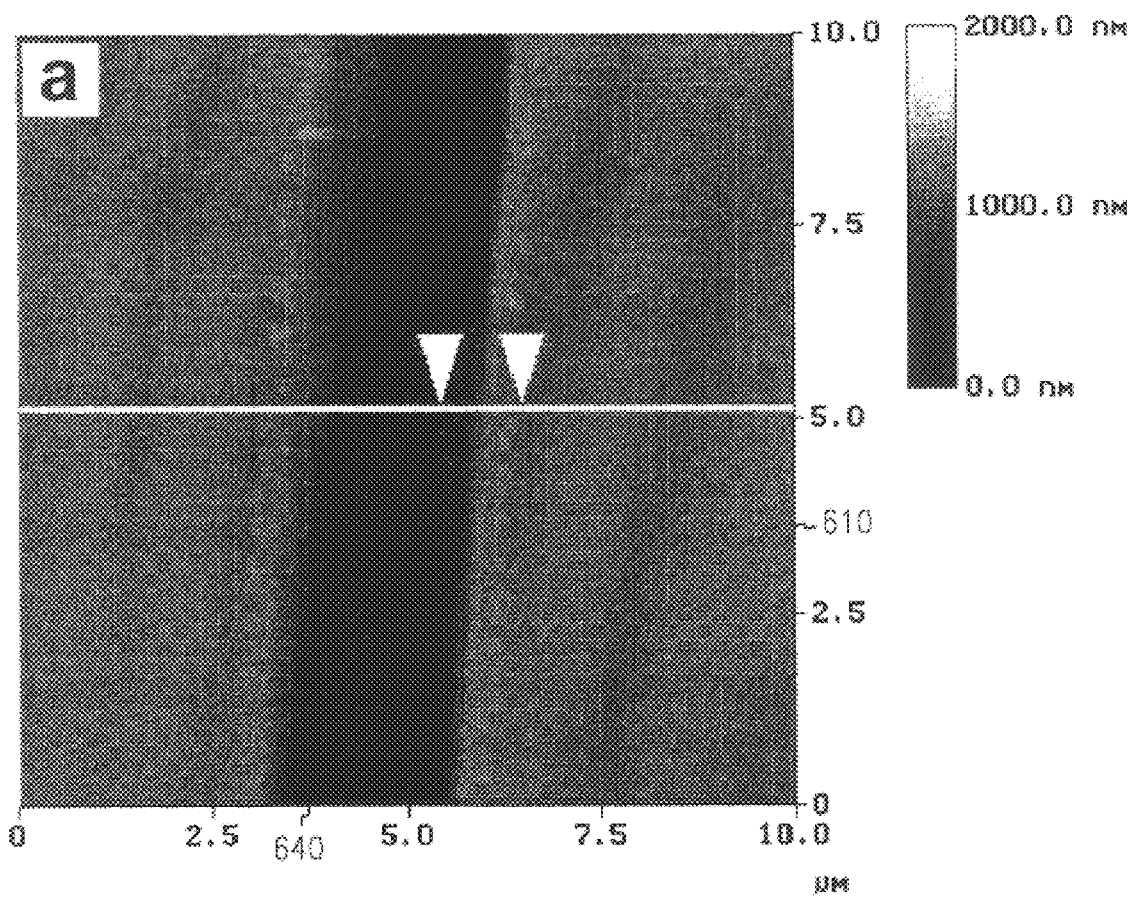
FIG. 7A is a 10 $\mu$m atomic force topograph of a patterned Parylene layer.
Figure 7B:
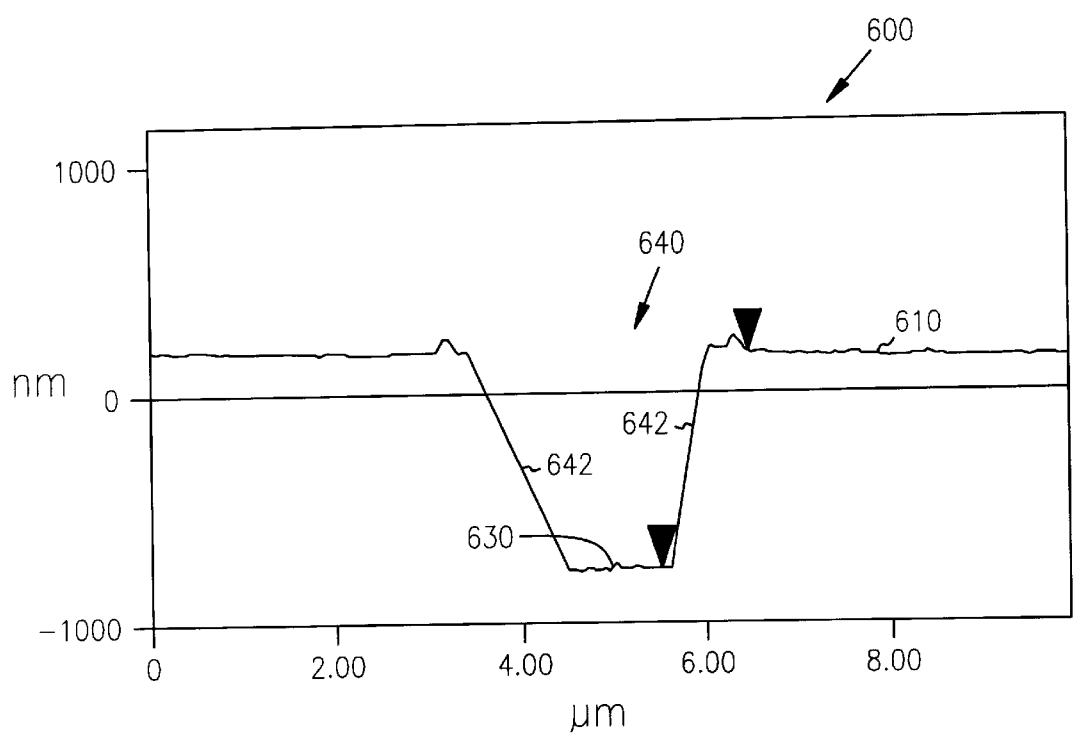
FIG. 7B is a scope trace showing a sectional profile taken across the channel of FIG. 7A.

FIG. 7A shows a 10 $\mu$m atomic force topograph of the lithographically patterned Parylene layer, and FIG. 7B is the corresponding scope trace showing a cross-sectional profile taken across this sample, where the arrows shown in the topograph correspond to the arrows represented in the cross-sectional profile. The polymer coating 610 is shown with the wall 642 defining the opening 640 and the portion 630 of the substrate 600 exposed through the opening 640. The image was acquired using a Digital Instruments Dimension 3000 atomic force microscope (AFM) in tapping mode using standard tapping mode silicon etch probes. The average thickness of the Parylene layer was 930±10 nm.

The patterned substrate was then covered with anti-*Escherichia coli* (*E. coli*) serotype O157:H7 antibodies (Kirkegaard & Perry Laboratories, Inc., Gaithersburg, Md.) (100 $\mu$l of *E. coli* serotype O157:H7 antibodies dispensed onto a single 1 $cm^2$ patterned wafer) and allowed to remain on the patterned substrate for 15 minutes. The patterned substrate was then rinsed with deionized water and dried under nitrogen gas.

The antibody layer is then contacted with *E. coli* cells at 530, so that the cells are adhered to the antibody layer. In the present example, 100 $\mu$l of a buffer solution containing *E. coli* cells (P. M. St. John et al., *Anal. Chem.*, 79, 1108 (1998)) was dispensed onto the patterned wafer and incubated at room temperature (25° C.) for 10 minutes. The substrate was rinsed, first in a 0.05% Tween□ solution to remove loosely bound cells and then in deionized water. The substrate where then dried under nitrogen gas.

Figure 6C:
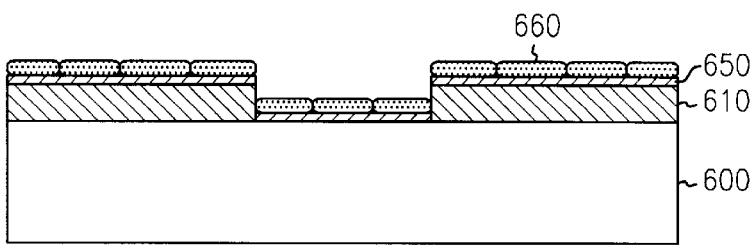
Figure 6D:
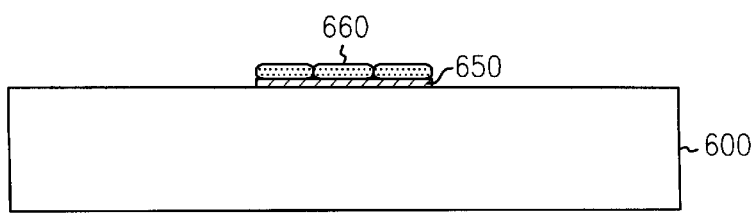

Referring again to the schematic illustrations of FIG. 6, FIG. 6C shows the silicon wafer substrate 600 and the polymer coating 610 after this process, where the antibody coating is shown generally at 650 and the *E. coli* cells are shown generally at 660. The Parylene coating was then peeled from the substrate, leaving the patterned antibody and *E. coli* layers on the surface of the substrate. FIG. 6D shows the substrate 600 with the patterned antibody and *E. coli* layers, 650 and 660, respectively. The resulting cell patterns were coated with a thin (<10 nm) Au/Pd layer to reduce charging effects during SEM.

Figure 8A:
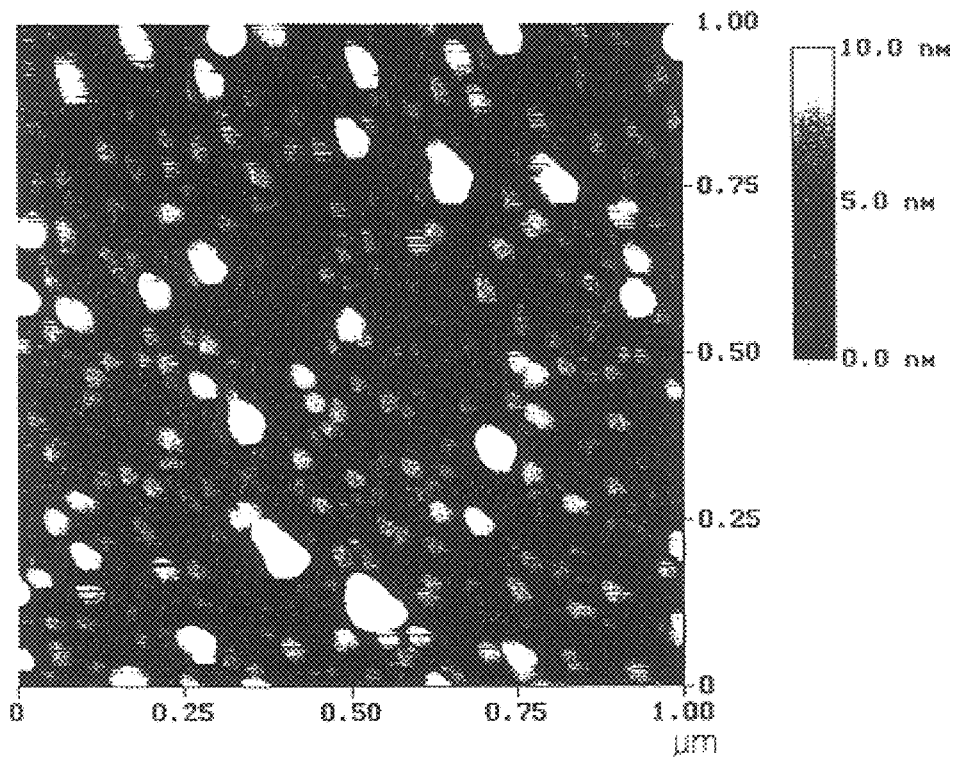
FIGS. 8A and 8B are atomic force topographs of bound *E. coli* cells on a silicon wafer prepared according to one embodiment of the present invention.
Figure 8B:
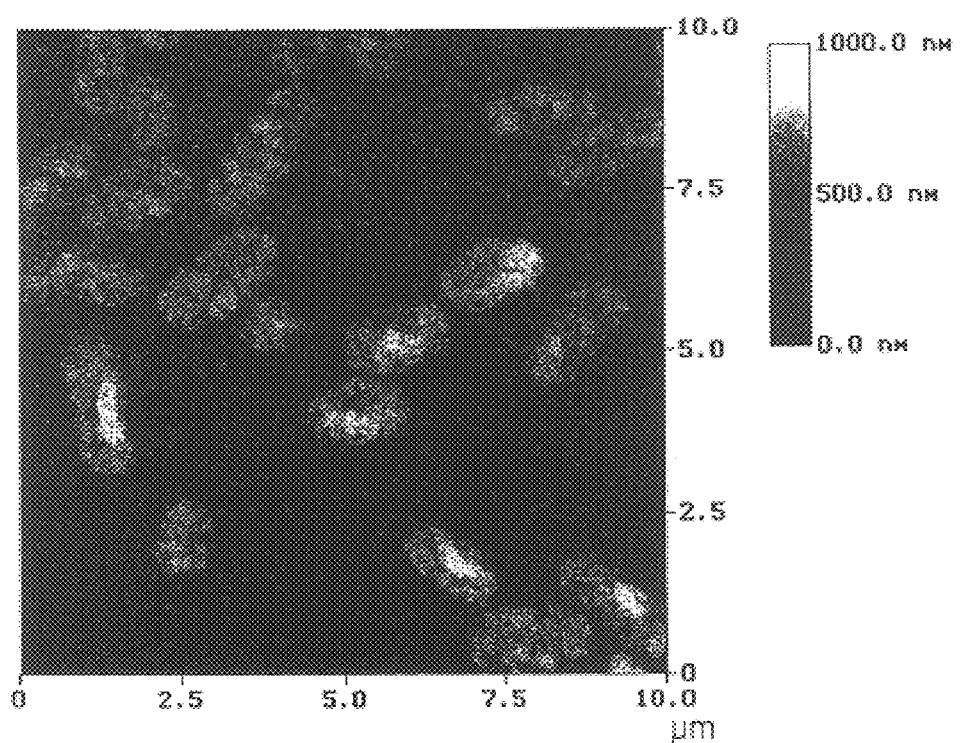

Scanning electron and atomic force microscopy were used to investigate the topography and morphology of various concentrations of patterned cells. FIGS. 8A and 8B show an atomic force topograph of a silicon wafer having a uniformly distributed immobilized peptide (*E. coli* antibody) layer and attached biological cells (*E. coli*), respectively. Scan sizes of the two images were 1 $\mu m^2$ (A) and 10 $\mu m^2$ (B) respectively and were both taken in tapping mode at a scan rate of 1 Hz. Tapping mode characterization eliminated the destructive lateral shear forces which can cause sample damage. The antibody layer was approximately 40 nm thick and appeared to be uniformly distributed throughout the sample region. The thickness of the antibody layer was determined by a surface scratching technique using a diamond coated tapping mode etched silicon probe.

Figure 9A:
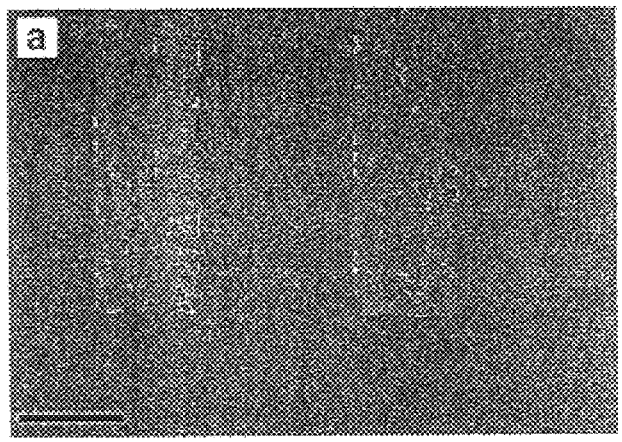
FIGS. 9A, 9B and 9C are scanning electron micrographs of a patterned antibody and *E. coli* layer on a silicon wafer prepared according to one embodiment of the present invention.
Figure 9B:
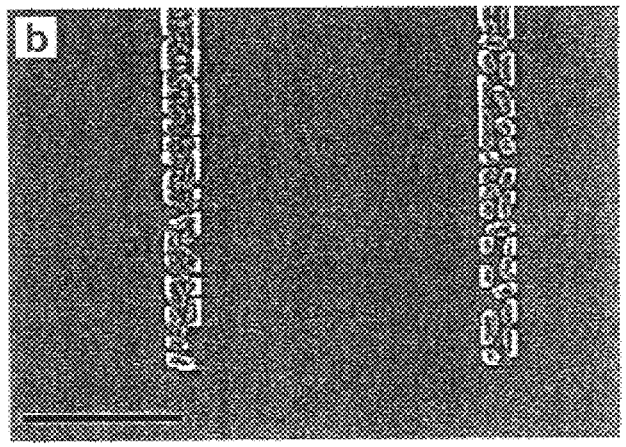
Figure 9C:
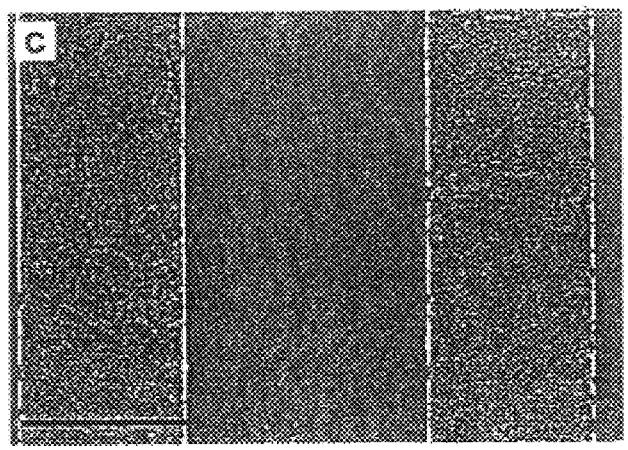

FIGS. 9A–9C are scanning electron micrographs (SEM) showing parallel channels containing antibodies, with attached *E. coli* cells. FIG. 9A is a SEM of 20 $\mu m$ wide lines of immobilized ant-*E. coli* antibodies and bound *E. coli* cells, deposited from a buffer solution containing $10^7$ suspended *E. coli* cells/ml. The light gray striped areas represent the region of antibody immobilization. Cell concentrations of $10^7$ cells/ml were used to fabricate the 5 millimeter long lines with a varying width from 2 $\mu m$ to 20 $\mu m$.

Morphological anomalies of the cell structure are apparent along the periphery of the confining channel region. Panels in FIGS. 9B and 9C are SEMs of 2 $\mu m$ and 20 $\mu m$ lines, respectively of immobilized antibodies and bound cells formed using a concentration of $10^9$ *E. coli* cells/ml. Micrograph 9B exemplifies the morphological edge distortions caused in the patterned cells (scale bare corresponds to 20 $\mu m$ in FIG. 9A, 10 $\mu m$ in FIG. 9B and 20 $\mu m$ in FIG. 9C.

Figure 10A:
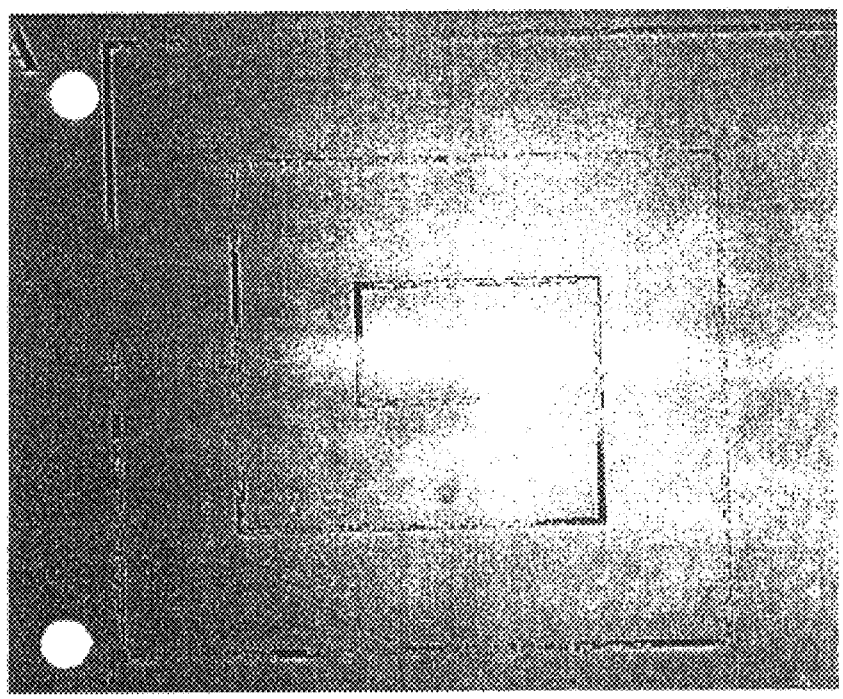
FIGS. 10A and 10B are scanning electron micrographs of patterned antibody and cell layer on a silicon wafer prepared according to one embodiment of the present invention.
Figure 10B:
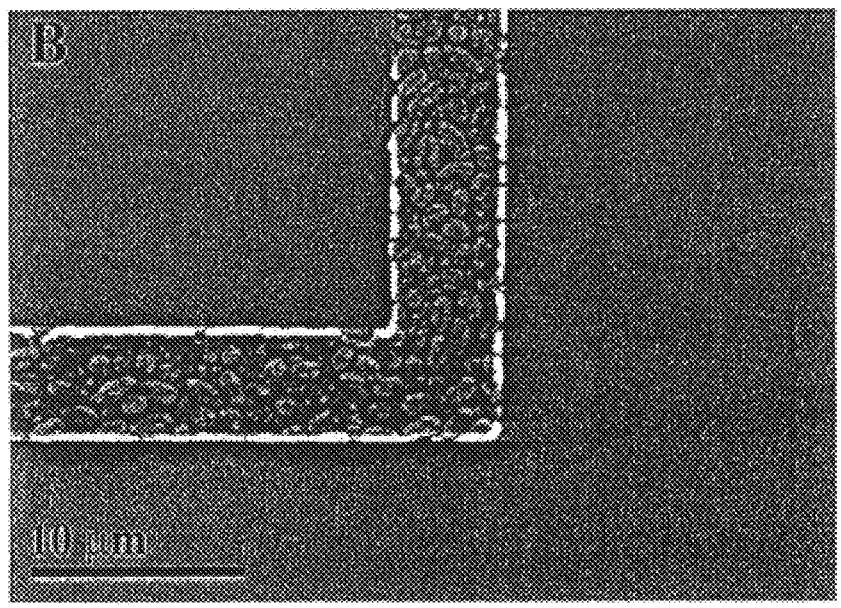

FIGS. 10A and 10B are examples of rectangular spirals created using the method of the present invention using an *E. coli* concentration of $10^9$ cells/ml (scale bar is 10 $\mu m$). More complex patterns of materials are also envisioned. For example, fabrication of regions of materials that have more than one intersection are possible.

EXAMPLE 2

Poly-L-lysine Deposition

Fluorescently labeled poly-L-lysine (P3069 Sigma-Aldrich, St. Louis, Mo.) was diluted in PBS to a concentration of 1 mg/ml. Silicon wafers patterned by the procedure of Example 1 were then immersed into the poly-L-lysine solution for 15 minutes. Samples were rinsed in deionized water and nitrogen dried. Parylene was then peeled and resulting patterns were imaged by fluorescence microscopy.

Figure 11A:
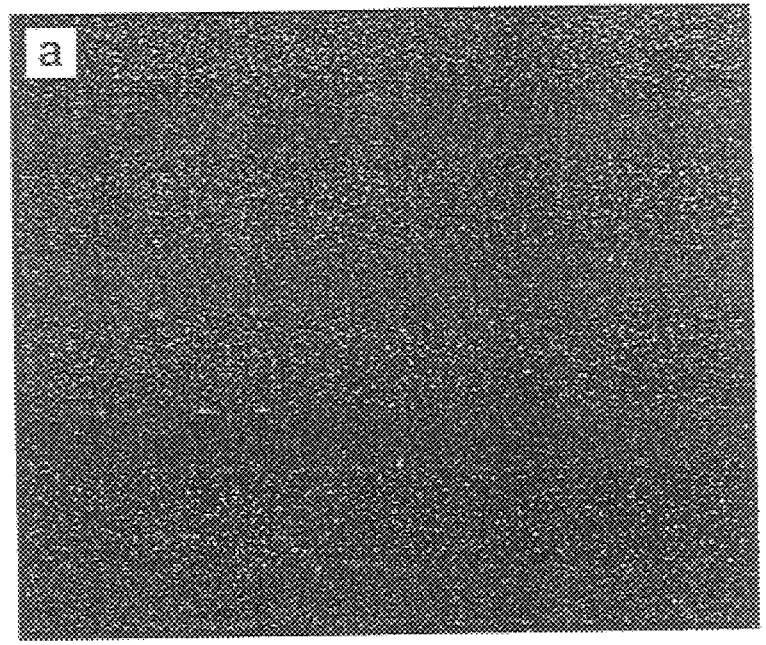
FIGS. 11A and 11B depict optical fluorescence characterization of patterned biologically sensitive, fluorescently labeled, immobilized layers.
Figure 11B:
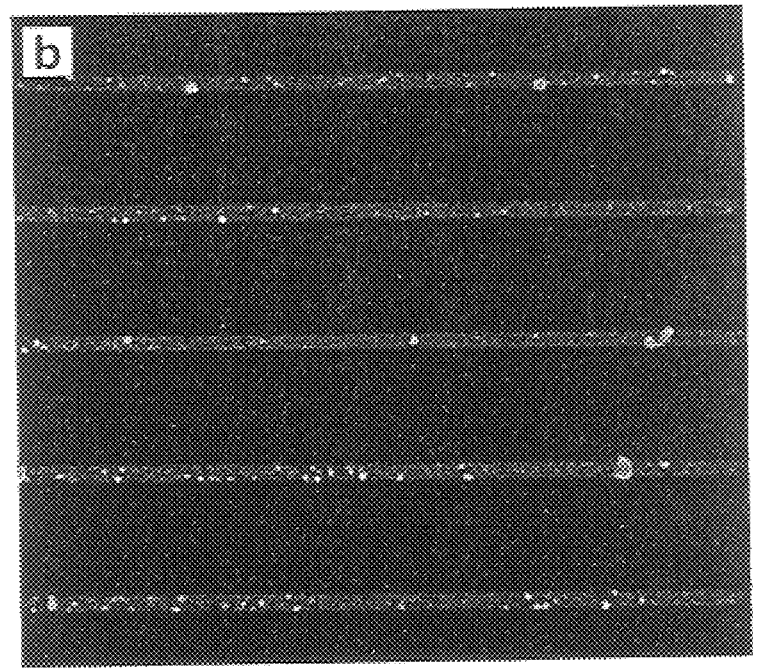

FIG. 11A shows patterned lines of fluorescently labeled poly-L-lysine. The lines are 20 $\mu m$ wide of fluorescently labeled poly-L-lysine. Fluorescence of the poly-L-lysine was quenched by the silicon as a result of a relatively thin silicon dioxide isolation layer. FIG. 11B shows 5 um wide lines of APTS functionalized with 20 nm aldehyde-sulfate fluorescent polystryrene spheres.

EXAMPLE 3

APTS Coating

Patterned wafers prepared as in Example 1 were first rinsed in acetone, then in isopropyl alcohol and then were nitrogen dried. Subsequently, the wafers were placed into boiling deionized water for 5 minutes, and then into a solution containing 1 ml APTS (aminopropyltriethoxysilane) (No. 80370, Pierce, Rockford, Ill.), 2 ml deionized water, 2 ml acetic acid, and 50 ml methanol for 15 minutes. The substrates were rinsed in methanol and nitrogen dried.

APTS patterned substrates were immersed into a solution containing 30 $\mu l$ of suspended 20 nm aldehyde-sulfate fluorescent polystyrene spheres (F8760 Green FluoSpheres from Molecular Probes, Eugene, Oreg.), 3 ml deionized water and 30 mg of MES buffer for 2 hrs. Substrates were then rinsed in deionized water and nitrogen dried. Parylene was peeled in a manner described above and the substrates were imaged using an optical fluorescent microscope. FIG. 11*b* shows patterned lines of APTS with attached 20 nm aldehyde-sulfate fluorescent polystyrene spheres, respectively.

EXAMPLE 4

RBL Cell Culturing

A subclone of Rat Basophilic Leukemia cells (RBL) (ATCC #C.RL-1378) was routinely passaged using Minimum Essential Medium, with Earle's Salts and L-glutamine (Gibco #11095), supplemented with 10% fetal bovine serum and 10% newborn calf serum (Gibco #26140 and 26010, respectively). Stocks were incubated at 37° C., in a humidified atmosphere, containing 5% $CO_2$ in air.

In preparation for seeding the cells on silicon surfaces, the wafers were washed with a stream of 70% ethanol in water, allowed to air dry in the sterile environment of a Baker laminar flow cabinet, and were placed in the bottom of 35 mm tissue culture dishes (Falcon part #35-1008). Stocks of adherent RBL cells were harvested by incubation with Trypsin-EDTA solution, and then diluted to an appropriate concentration with media. Concentrations of cells were confirmed by counting fractions of the stock using a Beckman-Coulter cell counter. Dishes were seeded with 10,000 to 30,000 cells and grown in the same conditions as the stocks for two to three days.

The culture dish was removed from the incubator and the access media was aspirated from the cells. 2 ml of 10 mM PBS was used to wash off the media proteins. 2 ml of 2% paraformaldehyde/PBS was added to the dish and allowed to fix for 15 minutes. The solution was aspirated, washed off with ethanol and allowed to air dry. Parylene was peeled and the samples were imaged using optical microscopy.

Figure 12:
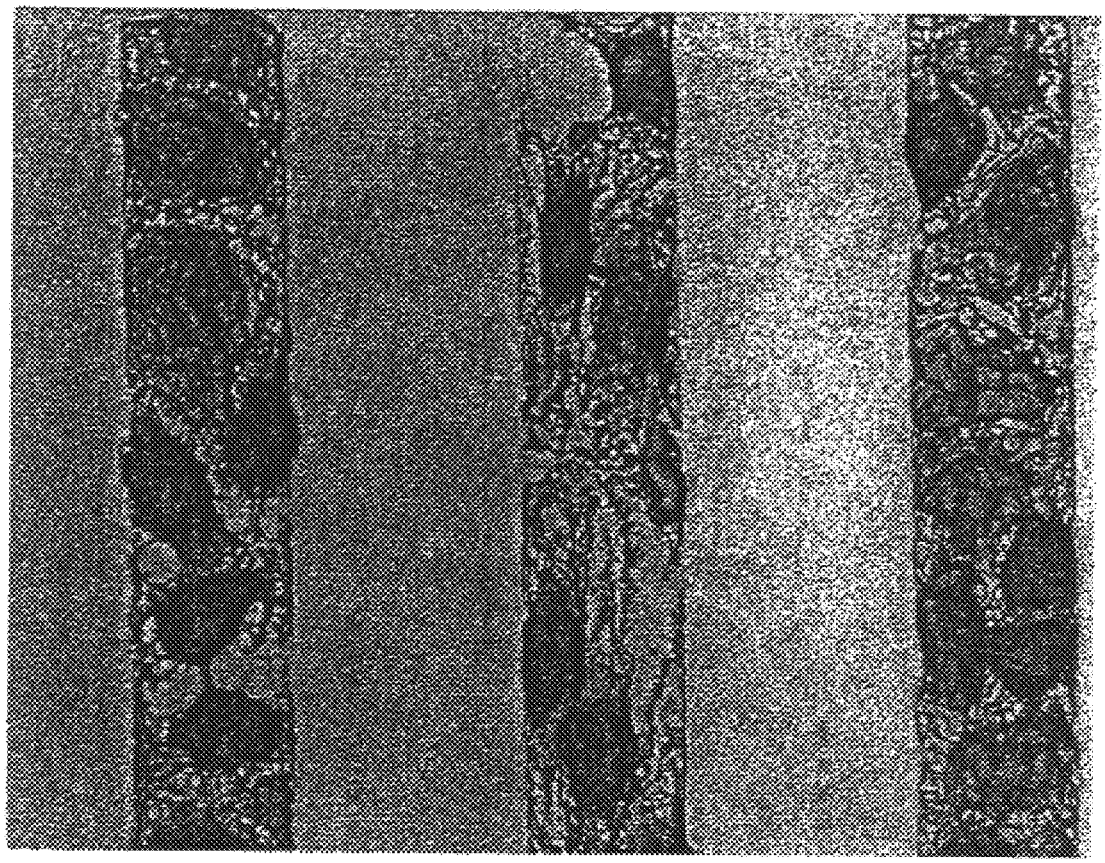
FIG. 12 is an optical micrograph of 20 $\mu$m lines of cultured RBL cells and the extracellular secretion matrix.

FIG. 12 shows an optical micrograph of 20 $\mu m$ wide lines of cultured RBL cells and their extracellular secretion matrix.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be! combined to form additional embodiments of the present invention. The scope of he invention should, therefore, be determined with reference to the appended claims, along with the full scope of equivalents to which such claims are entitled.

All publications cited herein are incorporated by reference as though fully set forth.

We claim:

1. An apparatus, comprising:
   a substrate;
   a polymer coating on a surface of the substrate, where the polymer coating is releasably attached to the substrate and has one or more predefined openings through which a portion of the substrate surface is exposed; and
   a layer of a preselected material on the polymer coating, wherein said layer also covers the portion of the substrate surface that is exposed through the predefined openings.

2. The apparatus of claim 1 wherein the material is a biological material.

3. The apparatus of claim 2 wherein the biological material is a polypeptide.

4. The apparatus of claim 2 wherein the biological material is a protein.

5. The apparatus of claim 2 wherein the biological material is an antibody or a subunit thereof.

6. The apparatus of claim 2 wherein the biological material comprises an antibody-antigen complex.

7. The apparatus of claims 1, 2, 3, 4, 5 or 6 wherein the polymer coating is removable to leave the preselected material on the substrate surface in a pattern of the predefined openings through the polymer coating.

8. The apparatus of claim 7 wherein the polymer coating can be removed from the substrate surface intact so as to leave the preselected material on the substrate surface in the pattern of the predefined openings through polymer coating.

9. The apparatus of claim 2 wherein the biological material comprises cells.

10. The apparatus of claim 9 wherein the cells comprise mammalian cells.

11. The apparatus of claim 9 wherein the cells comprise bacterial cells.

12. The apparatus of claim 2 wherein the biological material promotes the adhesion of cells.

13. The apparatus of claim 9 wherein predefined openings conform to the diameter of the cells.

14. The apparatus of claim 1 wherein the polymer coating is a polyaromatic polymer.

15. The apparatus of claim 14 wherein the polyaromatic polymer is Parylene.

16. The apparatus of claim 1 wherein the substrate surface comprises silicon, glass, ceramic, plastic, semi-conductor or metal.

17. The apparatus of claim 1 wherein the predefined openings are etched into the polymer coating.

18. The apparatus of claim 17 wherein the substrate surface that is exposed through the predefined openings is etched so as to increase the adhesion of the biological material thereto.

19. The apparatus of claim 1 wherein the polymer coating has walls along the predefined openings in the polymer coating, where the walls define a pattern for the layer on the substrate surface.

20. The apparatus of claim 1 wherein predefined openings have a width of at least about 0.1 $\mu$m.

21. The apparatus of claim 1 wherein the material is a metal.

* * * * *